United States Patent [19]

Lowery et al.

[11] Patent Number: 5,134,103
[45] Date of Patent: Jul. 28, 1992

[54] PROCESS FOR MAKING MAGNESIUM OXIDE SPHERES

[75] Inventors: Richard E. Lowery, Muscatine, Iowa; James L. Wright, Bartlesville, Okla.

[73] Assignee: Phillips Petroleum Company, Bartlesville, Okla.

[21] Appl. No.: 650,132

[22] Filed: Feb. 4, 1991

[51] Int. Cl.$^5$ .................. B01J 21/10; B01J 35/08
[52] U.S. Cl. .................................. 502/8; 502/340
[58] Field of Search ............ 502/8, 340; 423/635, 423/636

[56] References Cited

U.S. PATENT DOCUMENTS

| | | | |
|---|---|---|---|
| 2,348,847 | 5/1944 | Pike | 23/201 |
| 3,145,183 | 8/1964 | Fisher | 252/477 |
| 3,326,636 | 6/1967 | Hubble et al. | 23/201 |
| 3,748,282 | 7/1973 | Evans | 502/324 |
| 3,965,240 | 6/1976 | Hughey | 423/155 |
| 4,075,311 | 2/1978 | Eustacchio | 423/636 |

FOREIGN PATENT DOCUMENTS 59-98728  6/1984  Japan .................. 502/340

OTHER PUBLICATIONS

Stiles, Alvin B. "Catalyst Manufacture: Laboratory and Commercial Preparations" (Boston: Butterworths, ©1983) pp. 78–79.

*Primary Examiner*—W. J. Shine
*Attorney, Agent, or Firm*—Richmond, Phillips, Hitchcock & Umphlett

[57] ABSTRACT

A method to prepare spherical particles comprising magnesium oxide and magnesium hydroxide, wherein said magnesium hydroxide acts as a binder and no extraneous binder is present.

6 Claims, No Drawings

PROCESS FOR MAKING MAGNESIUM OXIDE SPHERES

This invention relates to magnesium oxide shaped particles.

BACKGROUND OF THE INVENTION

Magnesium oxide (MgO) is often used in a catalyst system as an isomerization catalyst or as a pretreatment agent in guard beds. For such use, the magnesium oxide requires processing. The processing is necessary because magnesium oxide is commercially available in the form of a very fine powder. This powder form of magnesium oxide lacks the practical physical characteristics magnesium oxide must have before use as a catalyst or pretreatment agent.

The magnesium oxide must be processed into shaped particles that exhibit attrition resistance before use as a catalyst or pretreatment agent. Such attrition resistance is often measured in terms of the crush strength of the particles. Adequate crush strength is necessary such that the magnesium oxide particles can withstand the pressure of hydrocarbon flow in the catalyst system as well as the stress placed on the particles when they are packed into a reactor or guardbed.

Extraneous binders have been employed as strength enhancers in magnesium oxide compositions used as catalyst particles. It is known in the art to prepare magnesium oxide tablets and extrudate by combining commercially available magnesium oxide powder with water and an extraneous binder such as silica. Other examples of extraneous binders used include clay, silica, alumina, and silica-alumina. Use of these binders, however, increases the cost of preparing the extrudate or tablets. Additionally, although most extraneous binders commonly used are considered inert, some of the binders may nevertheless alter the desired activity of the catalyst system.

SUMMARY OF THE INVENTION

It is an object of this invention to provide an economical and novel magnesium oxide catalyst.

It is a further object of this invention to provide an improved process for preparing a magnesium oxide catalyst.

It is a further object of this invention to provide an improved catalyst system for the isomerization of olefins.

It is a further object of this invention to provide an improved pretreatment agent for olefin reactions.

It is a further object of this invention to provide an improved process for the isomerization of olefins.

It is still a further object of this invention to prepare magnesium oxide spherical particles having good crush strength without the use of an extraneous binder.

In accordance with the invention, a process has been discovered for making spherical particles comprising the following steps in the order named:
(a) placing water and magnesium oxide on a rotating disk;
(b) rotating said disk to form spherical particles;
(c) drying said particles; and
(d) calcining said dried particles at a time and temperature sufficient to form spherical particles comprising magnesium oxide and magnesium hydroxide, wherein no extraneous binder is present.

DETAILED DESCRIPTION OF THE INVENTION

The present invention provides a method for preparing spherical particles of sufficient crush strength for use as a catalyst or pretreatment agent by contacting magnesium oxide powder and water on a rotating disk, rotating said disk to form spherical particles, drying said particles, and calcining said dried particles at a time and temperature sufficient to form spherical particles comprising magnesium oxide and magnesium hydroxide, wherein no extraneous binder is present. The need for an extraneous binder is eliminated because the final spherical particles include the presence of magnesium hydroxide in addition to magnesium oxide. The magnesium hydroxide acts as a strength enhancing agent in the particles. The calcining time of the spherical particles is directly related to how much magnesium hydroxide is left in the spherical particles, as explained in more detail hereinafter.

According to the invention, magnesium oxide powder is contacted with water on a rotating disk. The magnesium oxide absorbs the water, and the magnesium oxide and water react together in a highly exothermic manner to form magnesium hydroxide as follows:

$$MgO + H_2O \rightarrow Mg(OH)_2 \uparrow$$

The formation of the semi-solid magnesium hydroxide is not immediate. A time window exists where the water and magnesium oxide react. It is during this time window that the spherical particles must be formed on the rotating disk.

Different commercial brands of magnesium oxide powder have different time windows before the magnesium oxide begins to substantially react with water. All brands of commercially available magnesium oxide may be used in this invention, although the process machinery for making the spheres must be time efficient if the commercial brand of magnesium oxide powder is determined to be highly reactive with water.

The rotation of the disk causes the magnesium oxide powder and water to form spheres. Once formed the spheres are generally discharged from the disk through various techniques, as known the the art. Control of sphere size, avoidance of non-cohesive layers on the spherical particles, and avoidance of buildup of slurry on the spherical particles have also been addressed in the art.

Typically, the rotating disk is found on a disk spherudizing table, also known as a disk pelletizer, as described in *Catalyst Manufacture: Laboratory and Commercial Preparations*, by Alvin B. Stiles (New York: M. Dekker, c1983) pp. 78–79, the disclosure of which is hereby incorporated by reference. This spherudizing table is a preferred piece of machinery to employ in practicing this invention. Generally the spherudizing table has a flat, circular disk with a lip perpendicularly attached around the circumference of the disk. The rotating disk operates on an angle, and as it rotates, smaller spheres used as the seed material are placed in the bottom part of the disc and a spray of water is sprayed onto the smaller particles. As the moisture in the slurry evaporates, the solids form a layer on the exterior of the spheres thereby increasing their diameter. As the spheres increase in size, they segregate into sections where the desired size spheres can be removed by specially-designed draw-off techniques. Scrapers are generally stationarily mounted above the disk.

The sphere diameter depends on the angular positioning of the disk. Generally, the a larger angle placement results in smaller sphere diameter. Preferably the angle at which the disk is rotated is between about 1° to 89°, more preferably between 5° to 30°, and most preferably between 6° to 20°. The disk rotation must be at a sufficient speed to form the spherical particles. Preferably the disk rotation speed is between 1 and 50 rotations per minute (RPM). More preferably the disk rotation speed is between 10 and 30 RPM, and most preferably between 15 and 20 RPM.

The diameter of the spherical particles can be adjusted to suit the use qualifications of the final spherical compositions and will generally range from about 1/24" to about 1" in diameter.

It is preferred that the final magnesium oxide sphere have a surface area of at least about 1 $m^2/g$, preferably, from about 1 $m^2/g$ to 200 $m^2/g$. An adequate surface area is required so that the final particles have sufficient active sites to function well in a catalyst system. As the surface area increases, the number of active sites for hydrocarbons to react with the magnesium oxide also increases. Relating to this, the pore volume of the particles also indicates the amount of active sites that are available when the spheres are used as catalysts. The preferred pore volume range for the extrudate is from 0.30 to 0.65 cc/g.

In accordance with this invention, preferably the ratio of water to magnesium oxide is employed within a range from about 0.5 to about 0.75 kg. of water/kg. of magnesium oxide, more preferably from 0.55 to 0.65 kg. of water/kg. of magnesium oxide. The ratio is set such that the magnesium oxide powder is moistened by the water adequately to allow formation of spheres but not so excessively such that the water and powder mixture lacks the consistency to hold a spherical shape. Because the water content is controlled, the resulting spherical particles have structural integrity. The spheres may be stored and transported before the steps of drying and calcining are performed.

The drying step is where the spherical particles are exposed to a less intensive heat than that of the calcining step. In the drying step, free water is substantially driven off and separated from the spherical particles at a relatively low temperature because the free water is not chemically bound as magnesium hydroxide. The length of the drying time is somewhat dependent upon the amount of free water in the spherical particles. It is important to adequately dry the spheres prior to calcining. The spheres will loose structural integrity if subjected to high calcining temperatures while still containing excessive free water. Accordingly, if the spheres are prepared with an amount of water on the higher end of the stated water to magnesium oxide ratio, they will require a longer drying period because more free water is present.

The preferred temperature of the drying occurs from about 135° C. to about 315° C. for a period from about 15 seconds to about 8 hours. In general, drying at higher temperatures requires a shorter drying period. For instance, there are ovens available with agitating beds having temperatures from 260° C. to 315° C. at the entry portion of the oven. The agitating beds are positioned at an angle thereby allowing the spherical particles to move gradually from the entry portion of the oven to the more intensive heat. For this type of oven, drying time occurs at the entry portion of the oven lasting approximately 15 seconds to 5 minutes, the spheres are dried by the time they reach the more intensive heat of the oven for the calcining step. Although an oven allowing for both drying and calcining in a continuous fashion is most convenient, the drying step may also occur in a separate oven.

The calcining step is where the magnesium hydroxide is partially removed from the spheres by dehydration. Calcining requires a higher temperature than drying. During the calcining step, a portion of the magnesium hydroxide converts back to magnesium oxide as follows:

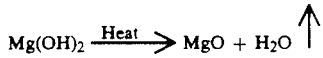

Because the main use of the spherical particles is to act as magnesium oxide catalysts, a substantial portion of the magnesium hydroxide must be converted to magnesium oxide or else the catalytic activity of the spheres will be poor.

The calcining temperature and time must be set to allow about at least 1 weight percent magnesium hydroxide to be left in the particles. In addition to the initial calcining of the spheres, separate activation of the spheres just prior to use in a reactor may include an additional calcining step. If this second calcining step is administered, care must be taken so that the total calcining time still allows for at least 1% magnesium hydroxide to be left in the spheres. If magnesium hydroxide content is driven off to below 1% of the spherical composition, the crush strength will not be adequate for usage as a catalyst.

Calcining should occur within a temperature range from about 425° C. to about 590° C. There are two preferred ranges for calcining time and temperature because intense heat allows for only a short exposure. Preferably calcining occurs within a higher temperature range from 451° C. to 590° C. for a time within the range from 0.5 to 2.0 hours or within a lower temperature range from 425° C. to 450° C. for a time within the range from 0.5 to 6.0 hours. More preferably calcining occurs within a temperature range from 500° C. to 575° C. for a period within the range from 0.5 to 2.0 hours. Most preferably calcining occurs at a temperature from 535° C.±5° C. for approximately 1 hour.

The magnesium hydroxide content is directly related to how much crush strength the spheres will exhibit. Crush strength measures the amount of weight that can be placed upon the particle before the particle loses structural integrity and crushes to form fines. A low crush strength (below 1 lb./in.) indicates that the particle is fragile and will not withstand much handling or hydrocarbon flow. Examining crush strengths in terms of magnesium hydroxide content shows that a high magnesium hydroxide content will yield spheres with high crush strength. Accordingly, a low magnesium hydroxide content will yield spheres with low crush strength. For use as an active catalyst, the magnesium hydroxide content must be high enough to allow for a crush strength greater than about 1 lb./in., preferably greater than 3 lbs./in. The magnesium hydroxide content must be greater than about 1 weight percent to yield a crush strength greater than 1 lb./in. The magnesium hydroxide content must be greater than about 5 weight percent to yield a crush strength greater than 3 lbs./in. Preferably the magnesium hydroxide content is present from about 5 to 35 weight percent in the sphere after calcining and activation (if activation is performed).

CATALYST SYSTEM

The magnesium oxide spheres make excellent catalysts in olefin isomerization reactions in addition to acting as excellent pretreatment agents in many different types of olefin reactions.

When using the magnesium oxide spheres as isomerization catalysts, olefins suitable for isomerization are those having from about 4 to about 30 carbon atoms and having at least one olefinic double bond and at least one allylic hydrogen atom, i.e., at least one hydrogen atom attached to a carbon atom adjacent to a double-bonded carbon atom. Exemplary compounds include, but are not limited to, acyclic and cyclic olefins such as 1-butene, 2,4,4-trimethyl-1-pentene, 1-pentene, 1-hexene, 2-hexene, 1-heptene, 3-heptene, the four normal octenes, the four normal nonenes and so forth; 3-methyl-1-butene, 3-methyl-1-pentene, 4-methyl-1-pentene, and the like, and mixtures of any two or more thereof. The isomerization products of these named olefins are the more thermodynamically stable structures whereby the double bond of the olefin has migrated closer to a more highly substituted carbon atom.

The isomerization reaction utilizing the magnesium oxide spheres may be run as a single reaction in a reactor or in conjunction with another reaction in the same reactor, such as running a disproportionation reaction with the isomerization reaction. Disproportionation occurs when a hydrocarbon converts into a similar hydrocarbon of either a higher or lower number of carbon atoms. The isomerization and disproportionation reactions are accomplished by using two appropriate catalysts. For example, when magnesium oxide spheres are combined with a disproportionation catalyst of tungsten oxide on a silica support, neohexene is produced. In this system 2,4,4-trimethyl-1-pentene is fed into a reactor, and the 2,4,4-trimethyl-1-pentene is isomerized to 2,4,4-trimethyl-2-pentene using the magnesium oxide spherical catalyst. Another feedstock, ethylene, is also fed into the reactor. The ethylene reacts with the isomerization product 2,4,4-trimethyl-2-pentene with the use of the disproportionation catalyst to form the neohexene.

Another process utilizing the magnesium oxide spheres as an isomerization catalyst and while also employing a separate disproportionation catalyst in the same reactor can be used to produce propylene. In this system 1-butene is fed into a reactor, and the 1-butene is isomerized to 2-butene. Another feedstock, ethylene, is also fed into the reactor. The ethylene reacts with the isomerization product 2-butene with the use of the disproportionation catalyst of tungsten oxide on silica support whereupon two units of propylene are formed.

The isomerization reaction conditions recommended when using the magnesium oxide spherical catalyst as compared to the magnesium oxide/extraneous binder tablet catalyst, which is known in the art, are essentially the same. The isomerization reactions can be accomplished at temperatures ranging from about 10° C. to about 590° C., preferably from about 150° C. to about 490° C. at any suitable pressure and at residence times throughout rates which will effect the desired degree of isomerization.

Before use in the isomerization catalyst system, the magnesium oxide spherical catalyst preferably is activated in a suitable manner such as by heating in a flowing stream of an oxygen-containing gas or in the presence of air. Because the magnesium oxide spheres must have a percentage of magnesium hydroxide of about 1% (preferably greater than 5%) present for purposes of maintaining strength, the activation should not be at high temperatures for extended periods, as previously explained.

After activation, sometimes it is advisable to flush the catalyst with an inert gas to remove any adsorbed oxygen or other gases from the magnesium oxide. The regeneration of spent magnesium oxide isomerization catalyst is generally accomplished by a technique which is similar to the activation of this material.

If a disproportionation catalyst is used, the proportion of magnesium oxide to disproportionation catalyst in the composite catalyst system can vary widely. At least about 0.1 part by weight of magnesium oxide should be present for each part by weight of disproportionation catalyst and there is no theoretical upper limit for the amount of magnesium oxide which can be present. Preferred ratios are 0.5 to about 20 parts by weight of magnesium oxide per part by weight of disproportionation catalyst. Equal parts of each catalyst give excellent results.

The conversion can be carried out at any convenient pressure up to about 2,000 psig or higher, preferably 0 to 500 psig, and at weight hourly space velocities (WHSV) of about 0.1 to about 1,000 w/w/hr. The mixed bed process can utilize any suitable contacting technique such as fixed bed reactors, fluidized bed reactors, suspended catalyst systems, and the like, and is effective with both gas phase and liquid phase operation. For example, for the conversion of normally liquid olefins, it is sometimes convenient to utilize a refluxing technique wherein the olefin charge is heated to boiling in a vessel on top of which is mounted a column containing the desired catalyst combination. The olefin vapors contact the catalyst and are converted to heavier olefins which are returned to accumulate in the vessel and to lighter olefins which rise to the top of the column. A condenser is used to return any unconverted olefin to the catalyst zone as a reflux while allowing the lighter product olefins to escape.

As previously indicated, the magnesium oxide spheres can also be used successfully as pretreatment agents in olefin reactions, including the olefin isomerization reactions utilizing magnesium oxide spheres as the isomerization catalyst. The purity of a feed is an important factor in olefin reactions. In some instances, it has been found that pretreatment of the olefin feed with activated magnesium oxide spheres at relatively low temperature is effective in improving the ease and efficiency of the subsequent olefin reaction. Activated magnesium oxide spheres are greatly superior to many other adsorption agents in the purification of feed streams for the olefin reaction. When used as a pretreatment agent the magnesium oxide spheres are generally placed in a guardbed. The olefin feed is exposed and thereby pretreated in the guardbed before it reaches the reactor where the desired olefin reaction occurs.

Magnesium oxide spheres can be used in conjunction with other known adsorptive materials in the pretreatment step where such materials are placed in a guardbed. For example, magnesium oxide can be used either consecutively or in mixture with alumina, silica gel, molecular sieve type materials, adsorptive clays, and the like. When used in mixture, the regeneration procedure should be selected to be compatible with all components of the treating mixture. In some instances, different regeneration techniques can be used, for example, treatment with polar solvents or by first segregating mechanically and isolating any temperature sensitive component for separate treatment.

The specific reasons why olefin pretreatment with the magnesium oxide is extremely beneficial in some instances is not known with certainty. However, it is believed that the olefin reaction process may be sensitive to such contaminants as peroxides and hydroperoxide compounds in very low concentration and that magnesium oxide is particularly effective in the removal of these and other impurities from olefins.

The invention is further illustrated, but not intended to be limited by, the following examples:

EXAMPLE 1

Spherical magnesium oxide particles were formed by contacting approximately 11.36 kgs of Combustion Engineers #98 P ® magnesium oxide with 6.818 kgs of distilled water, with a ratio of water to magnesium oxide of 0.6 kg water/kg. of magnesium oxide. The magnesium oxide powder was placed in a vibrator feeder (FMC Model F-T01) of a Spherudizer Table manufactured by Dravo Corporation (Model W-3707-4) and the water was placed in a holding tank. The water spray was set at 0.6 times the magnesium oxide feed rate. Upon activating the spherudizing table, the rotating disc angle was set at 10°, and the disc rotating speed was set at 20 RPM.

After approximately 5 minutes, ¼" diameter spheres were formed and removed from the spherudizing table and dried at approximately 300° F. (149° C.) in a Lindberd ® oven (Model 51441).

After drying, several sample spheres were measured for liquid pore volume and crush strength. The liquid pore volume value measured 0.613 cc/g, with the value being determined by the volume of toluene absorbed by the sphere. The crush strength value measured 10.4 lbs. and was determined by taking the means of 50 reading measuring the force required to crush 50 different spheres. The readings were taken by placing each sphere perpendicularly to the direction of the cylinder exerting force, with the reading indicating the amount of force required to crush the sphere. The instrument employed was a Model Accer Force ® II 100, Manufactured by Ametek, Mansfield & Green.

After drying, the spheres were calcined in three different batches in the Lindberg oven. The first batch, designated Catalyst A, were calcined at 538° C. for 8 hours. The second batch, designated Catalyst B, were calcined at 500° C. for 1 hour. The third batch, Catalyst C, were not calcined until just prior to placement into the reactor.

Liquid pore volume and crush strength values were measured for Catalysts A and B with the same procedure described above. Catalyst A had a pore volume of 0.83 cc/g and a crush strength mean value of 1.25 lbs. Catalyst B had a pore volume of 0.78 cc/g and a crush strength mean value of 7.68 lbs.

A comparison of the crush strength data of Catalysts A and B indicates a longer calcining time and higher calcining temperature results in making the spherical particle weaker.

The spherical particles designated Catalyst C were measured for catalytic activity in the isomerization of the olefin 4-methyl-1-pentene (4MP1) into 4-methyl-2-pentene (4MP2). The isomerization reaction was carried out by first activating 15 grams of the spheres in a tube reactor at 450° C. for 4 hours in the presence of dry nitrogen. The reactor design allowed for the olefin feed, 4-methyl-1-pentene, to first pass through a flow meter to a small, positive displacement pump, then onto the top of the loaded ⅜"×22" s./s. tube reactor which was jacketed by a heater. The temperature setting of the heater provided control for the reactor temperature. The temperature of the reactor was periodically increased 150° C. to 250° C. The olefin feed rate was 2 ml/minute. The reaction pressure was maintained at 100 psig.

The reaction products exited the bottom of the reactor to a back pressure regulator which dumped the product into a receiver for analysis by gas chromatography. The analysis of the product appears in Table 1 indicates the percentage of isomerization occurring at different reactor times and temperatures.

The products indicating isomerization activity are 4-methyl-2-pentene (4MP2) and 2-methyl-2-pentene (2MP2), where the double bond has migrated to a more thermodynamically stable position. The weight percentage values for both of these isomerized products indicate a high catalytic activity of the MgO spheres.

TABLe I

| | Isomerization Activity of Catalyst C Olefin Feed: 4-Methyl-1-Pentene | | | |
|---|---|---|---|---|
| Product Weight Percentage | Time: 2.0 Hr Temp: 164° C. | Time: 3.0 Hr Temp: 199° C. | Time: 5.0 Hr Temp: 199° C. | Time: 7.0 Hr Temp: 249° C. |
| 4MP1 | 5.83 | 3.36 | 3.04 | 2.28 |
| 4MP2 | 55.33 | 36.82 | 36.61 | 22.57 |
| 2MP1 | 4.70 | 12.89 | 13.33 | 18.43 |
| 2MP2 | 28.69 | 45.12 | 46.00 | 55.94 |
| Other | 5.08 | 1.81 | 1.02 | .78 |
| Total | 99.63* | 100 | 100 | 100 |

*Total weight percentage indicates slight error in gas chromatography reading.

That which is claimed is:

1. A process for making spherical particles consisting essentially of the following steps in the order named:
   (a) placing water and magnesium oxide on a rotating disk;
   (b) rotating said disk to form spherical particles;
   (c) drying said particles; and
   (d) calcining said dried particles at a time and temperature sufficient to form spherical particles consisting essentially of magnesium oxide and magnesium hydroxide, wherein no extraneous binder is present.

2. A process according to claim 1 wherein in step (a) said water and said magnesium oxide are present in a ratio from about 0.5 to about 0.75 kg. of water/kg. of magnesium oxide; in step (c) said drying occurs at a temperature from about 135° C. to about 315° C. for a period of about 15 seconds to about 8 hours; and in step (d) said calcining temperature is within the range from about 425° C. to about 590° C.

3. A process according to claim 2 wherein in step (a) said water and said magnesium oxide are present in a ratio from 0.5 to 0.7 kg. of water/kg. of magnesium oxide; and in step (d) said calcining time is within the range of 0.5 to 6.0 hours at said calcining temperature of 425° C. to 450° C.

4. A process according to claim 3 wherein in step (a) said water and said magnesium oxide are present in a ratio of 0.55 to 0.65 kg. of water/kg. of magnesium oxide.

5. A process according to claim 2 wherein in step (a) said water and said magnesium oxide are present in a ratio from 0.5 to 0.7 kg. of water/kg. of magnesium; and in step (d) said calcining time is within the range of 0.5 to 2.0 hours and said calcining temperature is within the range of 451° C. to 590° C.

6. A process according to claim 5 wherein in step (a) said water and said magnesium oxide are present in a ratio from 0.55 to 0.65 kg. of water/kg. of magnesium oxide; and in step (d) said calcining time is approximately 1 hour and said calcining temperature is within the range of 535° C.±5.

* * * * *